(12) United States Patent
Jeong et al.

(10) Patent No.: US 11,931,490 B2
(45) Date of Patent: Mar. 19, 2024

(54) AIR PURIFICATION MODULE AND REFRIGERATOR COMPRISING THE SAME

(71) Applicant: SEOUL VIOSYS CO., LTD., Gyeonggi-do (KR)

(72) Inventors: Jae Hak Jeong, Gyeonggi-do (KR); Ji Won Kim, Gyeonggi-do (KR); Sang Cheol Shin, Gyeonggi-do (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 376 days.

(21) Appl. No.: 17/221,413

(22) Filed: Apr. 2, 2021

(65) Prior Publication Data

US 2021/0220508 A1 Jul. 22, 2021

Related U.S. Application Data

(63) Continuation of application No. PCT/KR2019/013012, filed on Oct. 4, 2019.

(30) Foreign Application Priority Data

Nov. 29, 2018 (KR) .................. 10-2018-0150412

(51) Int. Cl.
*A61L 9/20* (2006.01)
*F24F 3/16* (2021.01)
*F24F 8/10* (2021.01)
*F24F 8/22* (2021.01)
*F25D 17/00* (2006.01)

(52) U.S. Cl.
CPC ................ *A61L 9/205* (2013.01); *F24F 3/16* (2013.01); *F24F 8/10* (2021.01); *F24F 8/22* (2021.01); *F25D 17/00* (2013.01); *A61L 2209/134* (2013.01); *A61L 2209/14* (2013.01); *F25D 2317/0417* (2013.01)

(58) Field of Classification Search
CPC ..... A61L 9/205; F24F 3/16; F24F 8/22; F24F 8/10

See application file for complete search history.

(56) References Cited

U.S. PATENT DOCUMENTS

2015/0064069 A1 3/2015 Yi et al.

FOREIGN PATENT DOCUMENTS

| CN | 1035438 A | 9/1989 |
| CN | 101371929 A | 2/2009 |

(Continued)

OTHER PUBLICATIONS

Extended European Search Report from European Patent Application No. 19869694.0 dated Sep. 29, 2022 (10 Pages).

(Continued)

*Primary Examiner* — Robert A Hopkins
(74) *Attorney, Agent, or Firm* — Perkins Coie LLP

(57) ABSTRACT

An air purification module for purifying air includes a photocatalyst filter and a light source unit sequentially arranged in a selected direction. The light source unit is spaced apart from the photocatalyst filter to provide light to the photocatalyst filter and includes a substrate and a light source disposed on the substrate. The substrate includes at least one aperture to control a flow channel and a flow velocity of air so as to improve air purification effects through the photocatalyst filter when the air flows from the substrate towards the photocatalyst filter.

17 Claims, 10 Drawing Sheets

(56) References Cited

FOREIGN PATENT DOCUMENTS

| CN | 101498487 A | | 8/2009 | |
| CN | 204128095 U | | 1/2012 | |
| CN | 102985116 A | | 3/2013 | |
| CN | 106839187 A | | 6/2017 | |
| CN | 206842184 U | | 1/2018 | |
| CN | 207221657 U | | 4/2018 | |
| CN | 207648958 | | 7/2018 | |
| CN | 108355491 A | * | 8/2018 | ............. F24F 13/28 |
| CN | 108883205 A | | 11/2018 | |
| JP | 2000116762 A | | 4/2000 | |
| JP | 2000257185 A | * | 9/2000 | |
| JP | 2001079072 | | 3/2001 | |
| JP | 2007120877 A | | 5/2007 | |
| JP | 2008104739 A | | 5/2008 | |
| JP | 2011096830 A | | 5/2011 | |
| JP | 2012-003907 A | | 1/2012 | |
| JP | 2012125756 | | 7/2012 | |
| JP | 2013-169408 A | | 9/2013 | |
| JP | 2015051268 | | 3/2015 | |
| JP | 2020000978 A | | 1/2020 | |
| KR | 20060042423 A | | 5/2006 | |
| KR | 10-2015-0028164 A | | 3/2015 | |
| KR | 1020170014483 | | 2/2017 | |
| KR | 10-2017-0022619 A | | 3/2017 | |
| KR | 20170062881 A | | 6/2017 | |
| WO | 2013018499 A1 | | 2/2013 | |
| WO | 2014156168 A1 | | 10/2014 | |
| WO | WO-2018141620 A1 | * | 8/2018 | ............. A61L 9/205 |

OTHER PUBLICATIONS

International Search Report for International Application PCT/KR2019/013012, dated Jan. 16, 2020.
Office Action issued in corresponding CN Application No. 201980003187.1, dated Jun. 27, 2022, 9 pages.
English Translation of Office Action from corresponding Japanese Patent Application No. 2021-518597, dated Jul. 4, 2023 (10 pages).
English translation of Korean Office Action from corresponding Korean Patent Application No. 1020180150412 dated Jun. 7, 2023 (7 pages).
English translation of Indian Office Action from corresponding IN Patent Application No. 202137020396 dated Dec. 15, 2022 (6 pages).
Office Action from corresponding Japanese Patent Application No. 2021-518597, dated Jan. 9, 2024.

* cited by examiner

AIR PURIFICATION MODULE AND REFRIGERATOR COMPRISING THE SAME

CROSS-REFERENCE OF RELATED APPLICATIONS AND PRIORITY

The Present Application is a continuation of PCT Application No. PCT/KR2019/013012 filed Oct. 4, 2019 which claims priority to Korean Applications Nos. 10-2018-0119725 filed Oct. 5, 2018 and 10-2018-0150412 filed Nov. 29, 2018, the disclosures of which are incorporated by reference in their entirety.

TECHNICAL FIELD

Embodiments of the present disclosure relate to an air purification module and a refrigerator including the same.

BACKGROUND

A refrigerator is a home appliance that includes a storage compartment adapted to store food in a refrigerated state and a cold air supply device adapted to supply cold air to the storage compartment to store the food in a fresh state.

Among foods stored in the refrigerator, some foods have various unpleasant odors including a fishy smell or a smell of fermented foods, such as kimchi. These odors can permeate into the refrigerator and cause discomfort to a user.

SUMMARY

Embodiments of the present disclosure provide an air purification module having improved deodorization efficiency.

In accordance with one aspect of the present disclosure, an air purification module adapted to purify air includes a photocatalyst filter and a light source sequentially arranged in a first direction. The light source is spaced apart from the photocatalyst filter to provide light to the photocatalyst filter and includes a substrate and a light emitting device disposed on the substrate. The substrate includes at least one aperture to control a flow channel and a flow velocity of air so as to improve air purification effects through the photocatalyst filter when the air flows from the substrate towards the photocatalyst filter, and the aperture has a diameter of 1.0 mm to 3.0 mm.

In at least one variant, the photocatalyst filter may have multiple through-holes parallel to the flow channel of the air and may be disposed parallel to the aperture of the substrate.

In another variant, the through-holes may pass through the photocatalyst filter and the aperture may pass through the substrate in the first direction.

In further another variant, assuming that a region which light emitted from the light emitting device reaches is referred to as an irradiation region, at least part of the photocatalyst filter may be disposed in the irradiation region.

In another variant, the aperture may be provided in plural and the substrate may include a heat dissipation portion disposed in a region between adjacent irradiation regions and having no apertures.

In another variant, the irradiation regions may be arranged in a matrix of rows and columns and the heat dissipation portion may be disposed between adjacent rows and between adjacent columns.

In another variant, the air purification module may further include a housing receiving the photocatalyst filter and the light source and having apertures through which the air flows in the first direction.

In another variant, the housing may include a rib disposed at a location corresponding to the heat dissipation portion.

In another variant, when viewed in the first direction, the substrate has a larger area than the photocatalyst filter and the photocatalyst filter may have a photocatalyst-facing region corresponding to the substrate and an outer region outside the photocatalyst-facing region.

In another variant, in the substrate, the aperture may be present in plural in each of the photocatalyst-facing region and the outer region and the apertures in the photocatalyst-facing region may have a larger size than the apertures in the outer region.

In another variant, in the substrate, the apertures may be present in the photocatalyst-facing region and may not be present in the outer region.

In another variant, the light source may be provided in plural. In some forms, the light source may include a first light source and a second light source facing each other with the photocatalyst filter interposed therebetween. In other forms, the light emitting devices of the first and second light sources may face each other with the photocatalyst filter interposed therebetween, and each of the first light source and the second light source may be provided with multiple apertures.

In another variant, when viewed in the first direction, the apertures of the first light source may be disposed to overlap the apertures of the second light source. Alternatively, when viewed in the first direction, at least some apertures of the first light source may be disposed so as not to overlap at least some apertures of the second light source.

In another variant, the apertures of the first light source may have a different size than the apertures of the second light source.

In another variant, when viewed in the first direction, the first light source and the second light source may include multiple regions at locations thereof overlapping each other and the light emitting devices may be disposed in at least one of the regions of the first light source and in at least one of the regions of the second light source.

In another variant, when viewed in the first direction, at least one of the regions of the first light source, in which the light emitting device is disposed, may not overlap at least one of the regions of the second light source, in which the light emitting device is disposed.

In another variant, in each of the first and second light sources, the apertures present in the regions in which the light emitting devices are disposed may have a different diameter than the apertures present in the regions in which the light emitting device is not disposed.

In another variant, in each of the first and second light sources, the apertures present in the regions in which the light emitting devices are disposed may have a larger diameter than the apertures present in the regions in which the light emitting device is not disposed.

In another variant, in each of the first and second light sources, a difference in area between the apertures present in the regions in which the light emitting devices are disposed and the apertures present in the regions in which the light emitting device is not disposed may be 20% or less.

In another variant, the air purification module may further include an air distributer disposed adjacent to the photocatalyst filter or the light source to supply the air at a uniform flow velocity and at a uniform flow rate towards the photocatalyst filter in the first direction.

In another variant, the air distributer may have pores through which the air passes. In one embodiment, the pores may have a smaller average diameter than the apertures of the substrate. In one embodiment, the air distributer may include at least one selected from among an organic antibacterial material and an inorganic antibacterial material.

Another aspect of the present disclosure relates to a refrigerator including the air purification module. The refrigerator includes: a main body provided with a cooling device and a storage compartment, and the air purification module disposed inside the storage compartment.

Embodiments of the present disclosure provide an air purification module having improved deodorization efficiency.

Embodiments of the present disclosure provide a refrigerator including the air purification module having improved deodorization efficiency.

In one or more embodiments according to the teachings of the present disclosure, an air purification module adapted to purify air includes a photocatalyst filter configured to purify air flowing therethrough, and a light source sequentially arranged relative to the photocatalyst filter in a selected direction. The light source is spaced apart from the photocatalyst filter and providing light to the photocatalyst filter. The light source includes a substrate and a light emitting device disposed on the substrate. The substrate includes at least one aperture having a diameter sized and varying to control a flow channel of air and a flow velocity of air to be uniform in response to a location of the light emitting device on the substate and an arrangement of the light source relative to the photocatalyst filter.

In at least one variant, at least part of the photocatalyst filter is disposed in an irradiation region to which light emitted from the light emitting device reaches.

In another variant, two or more apertures are provided and each aperture having a diameter ranging from 1.0 mm to 3.0 mm. The substrate further comprises a heat dissipation portion disposed between adjacent irradiation regions and having no aperture. The irradiation regions are arranged in a matrix of rows and columns such that the heat dissipation portion is disposed between adjacent rows and between adjacent columns.

In further another variant, the apertures of the first light source have a different size than the apertures of the second light source.

In one or more embodiments according to the teachings of the present disclosure, an air purification module adapted to purify air includes a photocatalyst filter configured to purify air flowing therethrough, and a light source including a first light source and a second light source facing the first light source. The photocatalyst filter is sandwiched between the first light source and the second light source such that the photocatalyst filter receives light from the first light source and the second light source. The first light source includes a first substrate and one or more first light emitting devices disposed on the first substrate. The second light source includes a second substrate and one or more second light emitting devices disposed on the second substrate. The first substrate includes at least one first aperture having a diameter sized and varying to control a flow channel of air and a flow velocity of air to be uniform in response to a location of the first light emitting device on the first substate and an arrangement of the first light source relative to the photocatalyst filter. The second substrate includes at least one second aperture having a diameter sized and varying to control a flow channel of air and a flow velocity of air to be uniform in response to a location of the second light emitting device on the second substate and an arrangement of the second light source relative to the photocatalyst filter.

In at least one variant, when viewed in a selected direction perpendicular to the first light source and the second light source, the first light source further comprises a first set of regions and the second light source further comprise a second set of regions, the first set of regions and the second set of regions corresponding to and overlapping with each other in the selected direction. The first light emitting devices are disposed in at least one of the first set of regions. The second light emitting devices are disposed in in at least one of the second set of regions. When viewed in the selected direction, said at least one of the first set of regions having the first light emitting device disposed, does not overlap said at least one of the second set of regions having the second light emitting device disposed.

In another variant, the first aperture further includes a third aperture present in said at least one of the first set of regions having the first light emitting devices disposed, and a fourth aperture present in another region of the first set of regions having no light emitting device.

The third aperture has a different diameter than the fourth aperture, and each of the third and the fourth apertures having a diameter ranging from 1.0 mm to 3.0 mm.

In further another variant, the diameter of the third aperture is larger than the diameter of the fourth aperture. A difference in area between the third aperture and the fourth aperture is 20% or less.

DETAILED DESCRIPTION OF EMBODIMENTS

The present disclosure may be implemented in various ways and certain embodiments will be described in detail with reference to the accompanying drawings. However, it should be understood that the present disclosure is not limited to the following embodiments and includes all modifications, variations, alterations, and equivalents within the spirit and scope of the present disclosure.

An air purification module according to embodiments of the present disclosure may be used in various air conditioners for refrigerators, automobiles, air cleaners, and the like. Fluid may include water or air and the air purification module according to the embodiments of the present disclosure means a device for treatment of air, such as sterilization, purification, deodorization, odor-masking, and the like. However, the air purification module according to the embodiments of the present disclosure is not limited thereto so long as the air purification module is applied to treatment of a certain fluid, such as sterilization, purification, deodorization, odor-masking, and the like. Further, the air purification module according to the embodiments of the present disclosure may be applied not only to air conditioners but also to other devices.

Hereinafter, embodiments of the present disclosure will be described in detail with reference to the accompanying drawings.

Figure 1:
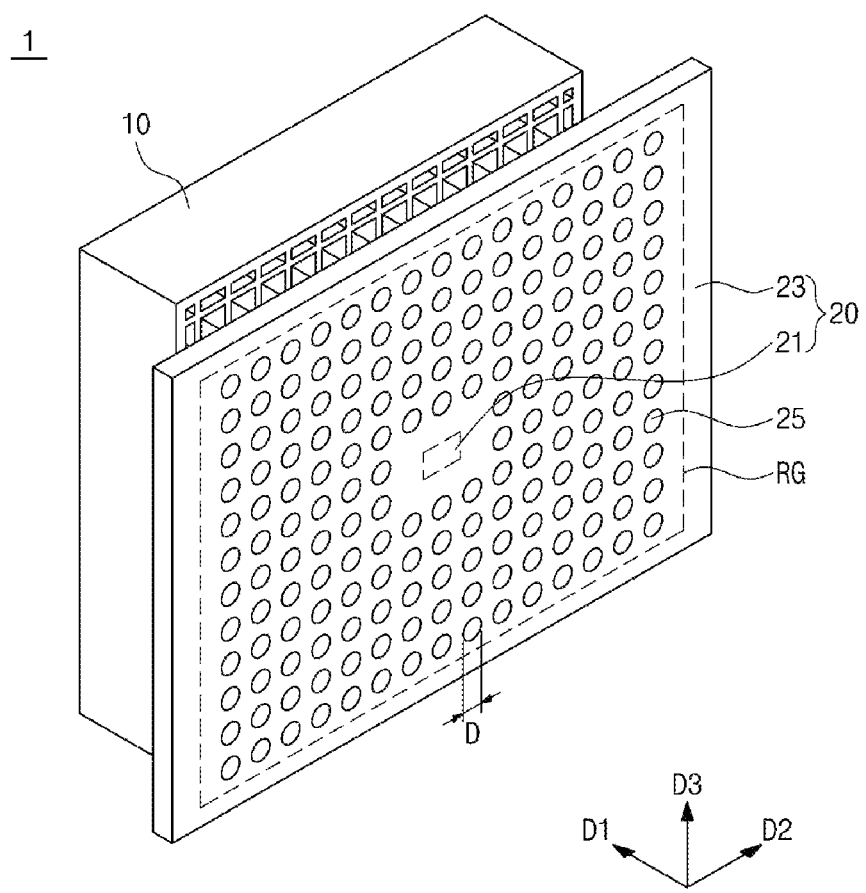
FIG. 1 is a perspective view of an air purification module according to an embodiment of the present disclosure.

FIG. 1 is a perspective view of an air purification module according to an embodiment of the present disclosure.

The air purification module 1 according to one or more embodiments of the present disclosure includes a photocatalyst filter 10 and a light source 20 emitting light to the photocatalyst filter 10. The light source 20 is spaced apart from the photocatalyst filter 10 and emits light to the photocatalyst filter 10.

The light source 20 includes a substrate 23 and a light emitting device 21 mounted on the substrate 23.

The substrate 23 may have a plate shape. The substrate 23 is spaced apart from the photocatalyst filter 10. The photocatalyst filter 10 and the substrate 23 are sequentially disposed in one direction. In the following, for convenience of description, a direction from the light source towards the photocatalyst filter will be defined as a first direction D1, a direction perpendicular to the first direction D2 and parallel to one surface of the substrate 23 will be defined as a second direction D2, and a direction perpendicular to the first and second directions D1, D2 will be defined as a third direction D3.

In this embodiment, the substrate 23 may have the same area as or a larger area than that of the photocatalyst filter 10.

In some forms, the substrate 23 of the light source 20 is formed with at least one aperture. Air to be deodorized or sterilized may be supplied at a suitable flow velocity and at a suitable flow rate to the photocatalyst filter 10 through the aperture.

As shown in FIG. 1, in the embodiment, the aperture may be provided in plural. The apertures 25 may be arranged in a matrix of rows and columns or may be randomly arranged.

In the embodiment, the apertures 25 are formed to pass through the substrate 23 such that air can flow to the photocatalyst filter 10 through the substrate 23. When the air flows to the photocatalyst filter 10 to increase a contact area between the air and the photocatalyst filter 10, an air purification effect of the photocatalyst filter 10 is improved. The apertures 25 serve to control a flow channel and the flow velocity of the air and may have various sizes. In one form, the apertures 25 may have a diameter D of about 1.0 mm to about 3.0 mm. Here, the diameters D of the apertures may be the same or different. When the apertures have different diameters D, the apertures may have an average diameter of about 1.0 mm to about 3.0 mm. If the diameter D of the apertures is less than about 1.0 mm, it can be difficult for air to pass through the apertures, thereby making it difficult to achieve effective deodorization and sterilization due to increase in pressure loss resulting from movement of the air. Further, if the diameter D of the apertures exceeds 3.0, it is difficult to control the flow velocity and flow direction of the air and the air tends to flow towards a certain portion in a certain direction, making it difficult to achieve uniform deodorization and sterilization.

The light emitting device 21 may be disposed on a surface of the substrate 23 facing the photocatalyst filter 10. Assuming that a region in which light emitted from the light emitting device 21 reaches is referred to as an irradiation region RG, at least part of the photocatalyst filter 10 is disposed in the irradiation region RG irradiated with light. In FIG. 1, for convenience of description, the irradiation region RG is indicated on the substrate 23 by a dotted line when viewed in the first direction D1. Since the light emitting device 21 is disposed on the substrate 23 and emits light towards the photocatalyst filter 10, an actual irradiation region is present at a side of the photocatalyst filter 10. In the following drawings, for convenience of description, the irradiation region RG is disposed on the substrate 23 when viewed in the first direction D1.

The irradiation region RG may have the same area as or a similar area to the photocatalyst filter 10 or may have a larger are than the photocatalyst filter 10 so as to cover the photocatalyst filter 10.

Light emitted from the light emitting device 21 may have wavelengths in various wavelength bands. Light emitted from the light emitting device 21 may have wavelengths in the visible wavelength band, in the IR wavelength band, or in other wavelength bands.

In one embodiment, the wavelength band of the light emitted from the light emitting device 21 may be changed depending upon a photocatalytic material provided to the photocatalyst filter 10 described below. The wavelength band of the light emitted from the light emitting device 21 may be set depending on a reaction wavelength band of the photocatalyst.

The light emitting device 21 may emit some fractions of the wavelength band depending on the photocatalytic material. In one form, the light emitting device 21 may emit light in the UV wavelength band, specifically in the wavelength band of about 100 nm to about 420 nm, more specifically in the wavelength band of about 240 nm to about 400 nm. In another form, the light emitting device 21 may emit light in the wavelength band of about 250 nm to about 285 nm and/or in the wavelength band of about 350 nm to about 280 nm. In further another form, the light emitting device 21 may emit light having a wavelength of 275 nm and/or 365 nm.

The light emitting device 21 may be selected from among any typical light emitting devices without limitation so long as the light emitting device can emit light in the wavelength band capable of reacting with the photocatalytic material. The light emitting device 21 may include a light emitting diode (LED). In some forms, the light emitting device 21 may emit light having a sterilization function in order to minimize proliferation of bacteria in addition to the light having the wavelengths mentioned above. For example, the light emitting device 21 may emit light in the wavelength band of about 100 nm to 280 nm corresponding to the UVC wavelength band. It should be understood that, in order to emit light in various wavelength bands, the light emitting device 21 may be selected from among other light emitting devices known in the art in addition to an LED.

However, it should be understood that the wavelength band of the light emitted from the light emitting device 21 is not limited thereto. In other embodiments, the light emitting device 21 may emit light not only in the UV wavelength band but also in the visible spectrum.

Figure 2:
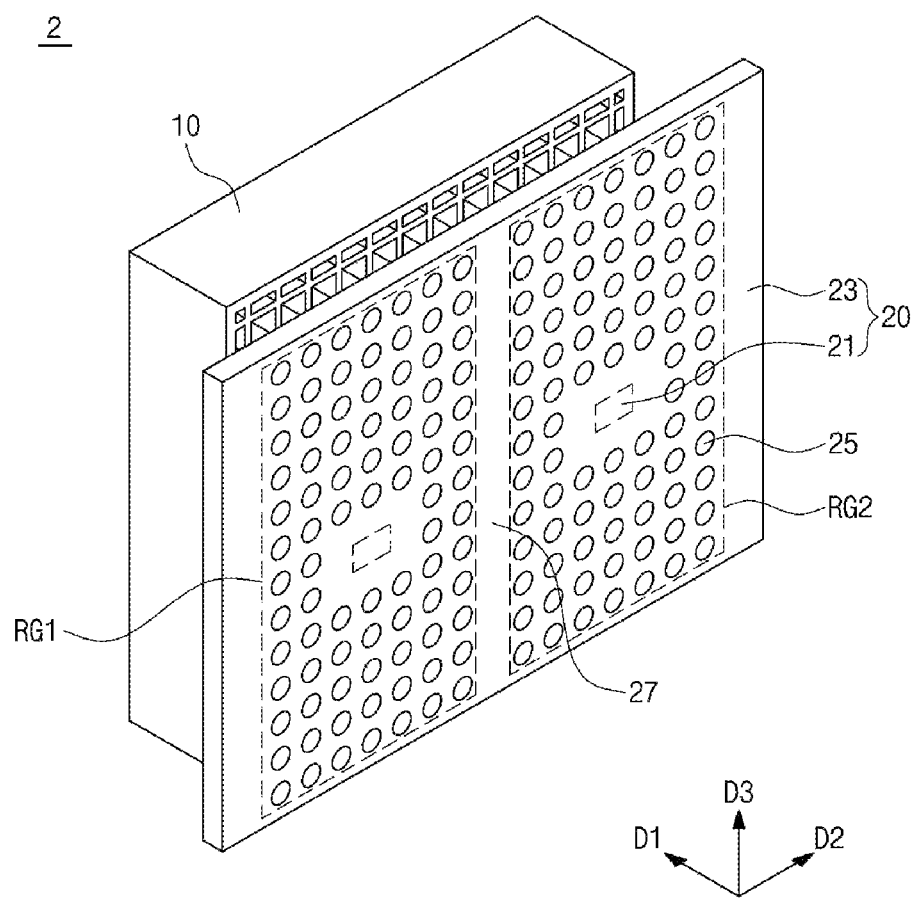
FIG. 2 is a perspective view of an air purification module according to another embodiment of the present disclosure, in which a light source is modified.
Figure 3:
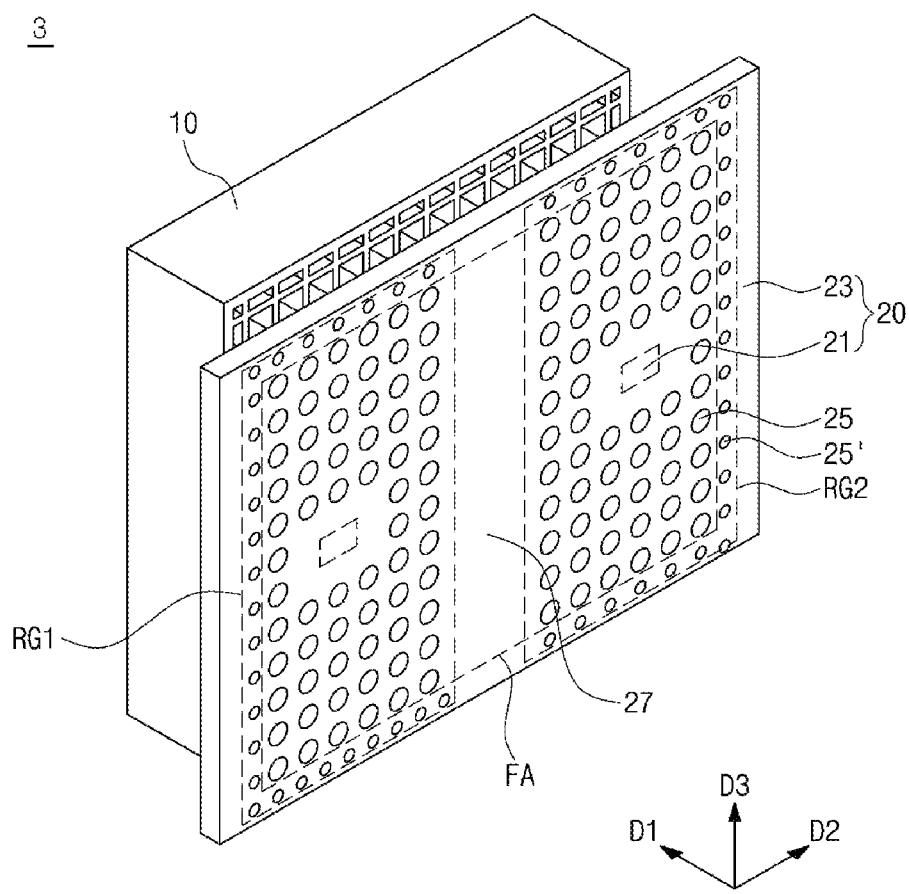
FIG. 3 is a perspective view of an air purification module according to further another embodiment of the present disclosure, in which the light source is modified.

In the embodiment, the light source 20 may emit in a direction in which the photocatalyst filter 10 is disposed, that is, in a direction facing one surface of the substrate 23. As shown in FIGS. 1-3, when the light emitting devices 21 are disposed on one surface of the substrate 23, the light emitting devices 21 may emit light in a direction perpendicular to the surface of the substrate 23 on which the light emitting devices 21 are disposed.

The photocatalyst filter 10 is spaced apart from the light source 20. The photocatalyst filter 10 is disposed in an air flow direction while being spaced apart from the light source 20, as shown in FIGS. 1-3. In one form, the photocatalyst filter 10 may have a rectangular parallelepiped shape having relatively large-area opposite surfaces. In one embodiment, the light source 20 is disposed on at least one of the opposite surfaces of the photocatalyst filter 10.

A flow channel is formed between the photocatalyst filter 10 and the light source 20 to allow air to flow between the photocatalyst filter 10 and the light source 20. Here, the air passes through the photocatalyst filter 10. That is, the opposite surfaces of the photocatalyst filter 10 may be perpendicular to the air flow direction, that is, the flow channel of the air.

The photocatalyst filter 10 may have a structure for maximizing the contact area with air. For example, according to one embodiment, the photocatalyst filter 10 may have a lattice shape, in which each of lattices is formed with a through-hole passing through the opposite surfaces of the photocatalyst filter 10. The through-holes of the photocatalyst filter 10 may be substantially parallel to the flow channel of the air. Further, the through-holes of the photocatalyst filter 10 may be substantially parallel to a direction in which the apertures 25 penetrate the substrate 23. For example, the through-holes of the photocatalyst filter 10 and the apertures 25 of the substrate 23 may be open at opposite sides thereof in the first direction D1. As a result, the flow channel may also be formed in the apertures 25 of the substrate 23 and in the through-holes of the photocatalyst filter 10. Here, the apertures 25 of the substrate 23 may not be completely parallel to the photocatalyst filter 10. That is, some apertures 25 of the substrate 23 may be generally parallel to the photocatalyst filter 10 and the other apertures 25 of the substrate 23 may not be parallel thereto so as to prevent generation of a zone causing stagnation of an air flow therein.

However, it should be understood that the shape of the photocatalyst filter 10 is not limited thereto and may be modified so as to increase the contact area with air. The photocatalyst filter 10 may be formed with multiple pores (not shown) therein, instead of the through-holes formed through the upper and lower surfaces thereof.

The photocatalyst filter 10 contains a photocatalyst that reacts with light emitted from the light source 20 to treat air.

The photocatalyst is a substance that causes catalytic reaction with light. The photocatalyst can react with light in various wavelength bands depending on substances constituting the photocatalyst. In the embodiment, a material causing photocatalytic reaction with light in the UV wavelength band among various wavelength bands may be used. However, the photocatalyst is not limited thereto and other photocatalysts having the same or similar mechanism may be used depending on light emitted from the light emitting device 21.

The photocatalyst is activated by UV light to cause chemical reaction, thereby decomposing various pollutants and bacteria in air, which contacts the photocatalyst, through redox reaction.

The photocatalyst causes chemical reaction generating holes and electrons when exposed to light having intensity greater than or equal to band-gap energy. As a result, compounds in air, for example, water or organic materials, can be decomposed by hydroxyl radicals and superoxide ions generated by photocatalytic reaction. The hydroxyl radicals are substances having very strong oxidation power and decompose organic contaminants in air or sterilize bacteria in air. Such a photocatalyst material may include titanium oxide ($TiO_2$), zinc oxide (ZnO), tin oxide ($SnO_2$), and the like. In one embodiment, since the recombination rate of electrons and holes generated on the surface of the photocatalyst is very high, there is a limit in use of the photocatalyst for photochemical reaction. Thus, metals, such as Pt, Ni, Mn, Ag, W, Cr, Mo, Zn, and the like, and oxides thereof may be added thereto in order to reduce the recombination rate of electrons and holes. If the recombination rate of holes and electrons is reduced, the possibility of contact with a target material to be oxidized and/or decomposed increases, thereby increasing reactivity of the photocatalytic material. In addition, an oxide may be added to the photocatalytic material to improve performance thereof through adjustment of a photocatalyst band gap. Air can be sterilized, purified, and deodorized through such photocatalytic reaction described above. In particular, for sterilization, the photocatalyst can promote sterilization or antibacterial reaction by destroying enzymes in cells of bacteria and enzymes acting on the respiratory system, thereby preventing propagation of bacteria or fungi while decomposing toxins released therefrom.

In particular, according to one embodiment, the photocatalyst may include titanium oxide ($TiO_2$). Upon irradiation with UV light having a wavelength of 400 nm or less, titanium oxide generates hydroxyl radicals and superoxide ions, which decompose organic substances into water and carbon dioxide through redox reaction. Titanium dioxide may be provided in the form of nanoparticles to generate a large amount of hydroxyl radicals even when the light emitting device emits light having a relatively weak UV wavelength. Therefore, the photocatalyst has excellent decomposition capability in decomposition of organic materials, exhibits continuous durability and stability despite environmental change, and can be semi-permanently used. Furthermore, hydroxyl radicals generated in large quantities can remove not only organic materials, but also various substances, such as odor-causing substances and bacteria.

In this embodiment, since the photocatalyst acts as a catalyst and does not change by itself, the photocatalyst can be used semi-permanently and can ensure that the effects of the photocatalyst are semi-permanently continued so long as light in a corresponding wavelength band is provided thereto.

With the structure described above, the air purification module 1 may maintain the flow velocity and flow rate of air supplied to the photocatalyst filter 10 through the apertures 25 of the substrate 23 of the light source 20 to secure deodorization by the photocatalyst filter 10. Further, the air purification module 1 may maintain the flow velocity and flow rate of air supplied to the photocatalyst filter 10 through the apertures 25 to be uniform on the photocatalyst filter 10. Accordingly, the air purification module 1 maximizes air sterilization and deodorization effects.

FIG. 2 is a perspective view of an air purification module 2 according to another embodiment of the present disclosure, in which the light source 20 is modified. The following description will focus on different features from those of the above embodiment as shown in FIG. 1 and the same components are indicated with the same reference numerals.

In the embodiment, the light emitting device 21 may be provided in plural. In this embodiment, the air purification module 2 includes two light emitting devices 21 by way of example. The number and arrangement of irradiation regions RG may be changed depending on arrangement of the light emitting devices 21. Thus, the light emitting devices 21 may be suitably disposed on the substrate 23 in consideration of the irradiation region RG. Here, each of the light emitting devices 21 may supply light to a first irradiation region RG1 and a second irradiation region RG2, as shown in FIG. 2.

When the light emitting devices 21 are provided in plural as in this embodiment, the light emitting devices 21 may be disposed in various ways such that the maximum area of the photocatalyst filter 10 can be irradiated with light emitted therefrom as uniformly as possible. Here, the light emitting devices 21 may emit light in the same wavelength band or in different wavelength bands. For example, in some embodiments, all of the light emitting devices 133 may emit light in the UV wavelength band. In other embodiments, some light emitting devices 21 may emit light in some fraction of the UV wavelength band and the other light emitting devices 21 may emit light in the other fraction of the UV wavelength band. By way of example, some light emitting devices 21 may emit light in the wavelength band of about 320 nm to about 400 nm and the other light emitting devices 21 may emit light in a different wavelength band.

In this embodiment, the quantity of light is relatively small between two adjacent irradiation regions RG. Accordingly, when air is supplied to a region between two irradiation regions RG, it can be difficult to achieve sufficient deodorization and sterilization and the apertures 25 may not be disposed between the two irradiation regions RG. Accordingly, the air purification module can reduce the amount of air in a region irradiated with a small quantity of light while promoting the air flow to a region sufficiently irradiated with light, thereby improving air deodorization and sterilization effects.

A region of the substrate 23 in which the apertures 25 are not present corresponds to a solid portion of the substrate 23 and has higher thermal conductivity than a region of the substrate 23 in which the apertures 25 are present. Accordingly, the region between two irradiation regions RG in which the apertures 25 are not present may act as a path along which heat generated from the light emitting devices 21 is easily transferred, that is, a heat dissipation portion 27. In other words, the heat dissipation portion 27 is a portion of the substrate 23 disposed in the region between the adjacent irradiation regions RG and corresponds to the region of the substrate 23 in which the apertures 25 are not present.

FIG. 3 is a perspective view of an air purification module according to further another embodiment of the present disclosure, in which the light source 20 is modified.

In one embodiment, the substrate 23 of the light source 20 may have a larger area than the photocatalyst filter 10. Accordingly, when viewed in the air flow direction, the substrate 23 may be provided with a region corresponding to one surface of the photocatalyst filter 10, that is, a photocatalyst-facing region FA of the substrate 23 directly facing the one surface of the photocatalyst filter 10, and an outer region not facing the one surface of the photocatalyst filter 10, which is a region outside of the photocatalyst-facing region FA.

In one embodiment, in order to improve air sterilization effects by allowing air to contact or pass through the photocatalyst filter 10, the photocatalyst-facing region FA of the substrate 23 facing the one surface of the photocatalyst filter 10 and the outer region may have different sizes or densities of the apertures.

For example, when each of the photocatalyst-facing region FA and the outer region is provided with multiple apertures 25, 25', the apertures 25 in the photocatalyst-facing region FA may have a larger size (for example, diameter) than the apertures 25' in the outer region. This structure is designed to allow a greater amount of air to flow in the photocatalyst-facing region FA than in the outer region. Alternatively, a frequency of direct contact between air and the photocatalyst filter is reduced in the outer region as compared with the photocatalyst-facing region FA. Formation of the apertures in the outer region may be omitted, and the outer region may not be provided with the apertures.

Further, in this embodiment, although the apertures disposed in the region FA facing the one surface of the photocatalyst filter 10 are illustrated as having the same size, it should be understood that the present disclosure is not limited thereto and the apertures may have a different diameter in a certain region.

In some forms, the apertures 25 in the photocatalyst-facing region FA may be present in a higher density than the apertures 25' in the outer region. This structure is designed to allow a greater amount of air to flow in the photocatalyst-facing region FA than in the outer region. Herein, the density of the apertures means an area ratio of the area occupied by the apertures to the entire area of the substrate.

Figure 4:
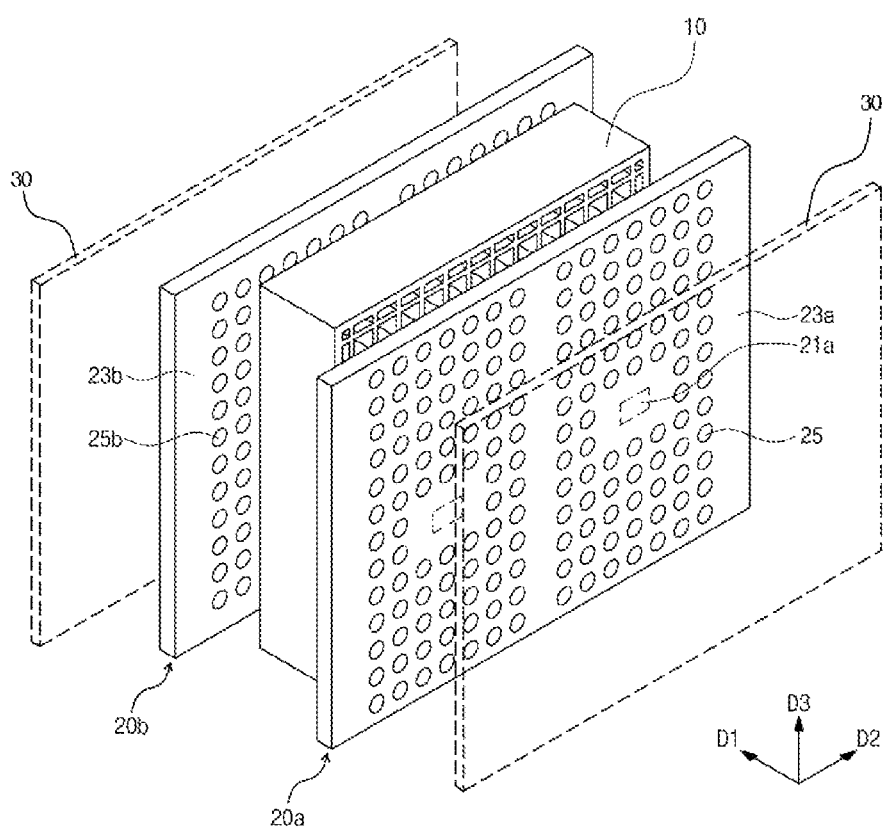
FIG. 4 is a perspective view of an air purification module according to further another embodiment of the present disclosure, in which multiple light sources are disposed.
Figure 5A:
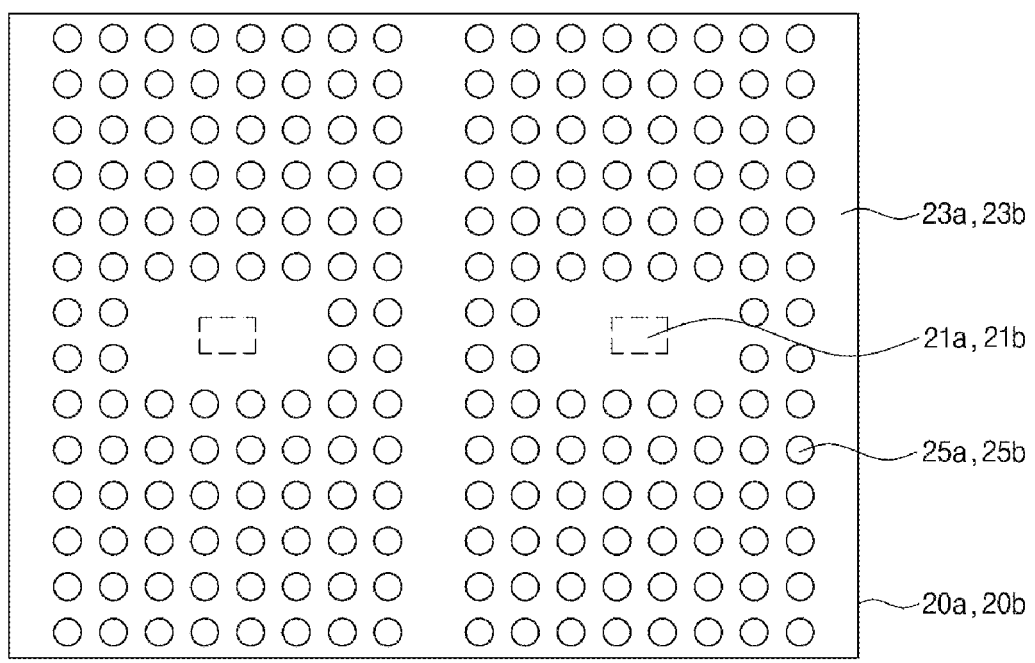
FIG. 5A is a plan view of the air purification module illustrating one arrangement of a first light source and a second light source shown in FIG. 4.
Figure 5B:
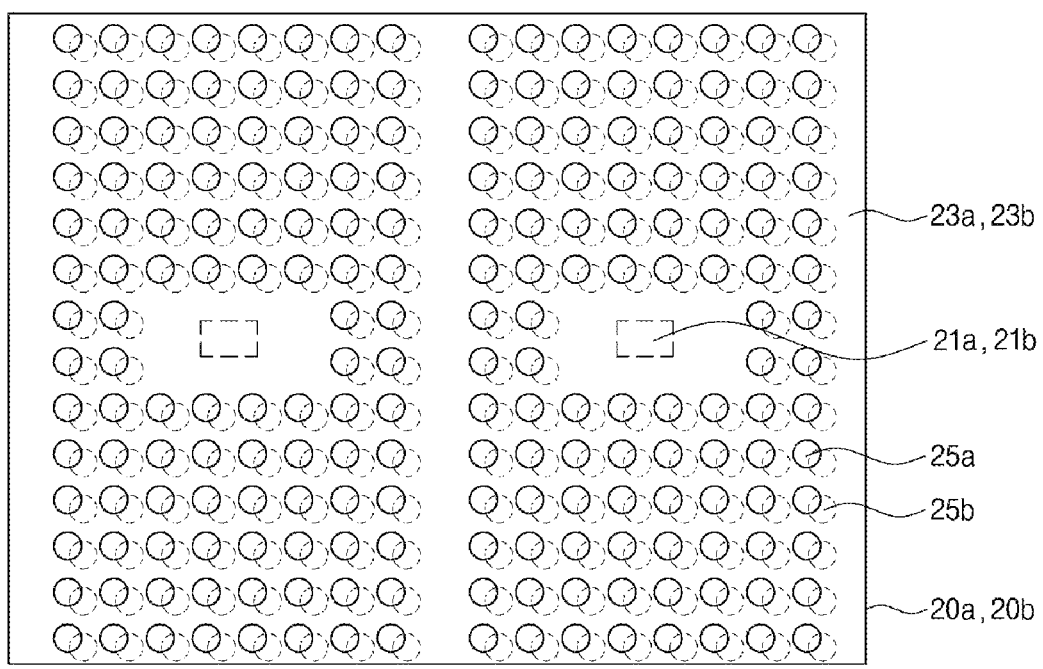
FIG. 5B is a plan view of the air purification module illustrating another arrangement of the first light source and the second light source shown in FIG. 4.

In some embodiments, components of the air purification module may be modified in various ways. For example, the light source may be provided in plural. FIG. 4 is a perspective view of an air purification module 3 according to another embodiment of the present disclosure, in which multiple light sources are disposed. FIG. 5A and FIG. 5B are plan views of the air purification module according to the embodiment of the present disclosure, illustrating light sources shown in FIG. 4.

Referring to FIG. 4, FIG. 5A and FIG. 5B, in the air purification module 3 of this embodiment, the light sources may be provided to one side of the photocatalyst filter 10 or to both sides of the photocatalyst filter 10. That is, a first light source 20a and a second light source 20b disposed to face each other with the photocatalyst filter 10 interposed therebetween may be provided as the light sources, as shown in FIG. 4.

The first light source 20a includes a first substrate 23a, first light emitting devices 21a mounted on the first substrate 23a, and first apertures 25a formed in the first substrate 23a to pass through opposite surfaces thereof. Referring to FIG. 5A and FIG. 5B, the second light source 20b includes a second substrate 23b, second light emitting devices 21b mounted on the second substrate 23b, and second apertures 25b formed in the second substrate 23b to pass through opposite surfaces thereof.

In this embodiment, the first light source 20a and the second light source 20b may be disposed to face each other. That is, the first light source 20a and the second light source 20b may be disposed to face each other such that the first light emitting devices 21a of the first light source 20a face the second light emitting devices 21b of the second light source 20b, with the photocatalyst filter 10 interposed therebetween.

In this embodiment, in order to allow air to efficiently pass through the first and second substrates 23a, 23b and the photocatalyst filter 10, the first and second apertures 25a, 25b may be parallel to the through-holes of the photocatalyst filter 10. That is, a direction in which the first and second apertures 25a, 25b are formed in the first and second substrates 23a, 23b may be parallel to the direction in which the through-holes are formed in the photocatalyst filter such that an air channel is formed. Accordingly, air can sequentially pass through the first apertures 25a of the first substrate 23a, the photocatalyst filter 10, and the second apertures 25b of the second substrate 23b while efficiently performing sterilization and deodorization.

Here, although light discharged from the first and second substrates 23a, 23b can travel in various directions, considering the fact that a large quantity of light travels perpendicular to one surface of each of the first and second substrates 23a, 23b, the light emitted from the light emitting devices 21 disposed on one surface of each of the first and second substrates 23a, 23b may effectively reach each portion of the photocatalyst filter 10, for example, a portion inside the through-holes.

Here, there can be a difference in flow velocity, flow rate and/or uniformity of air according to devices employing the air purification module, and the flow velocity, flow rate and/or uniformity of the air may be efficiently controlled through adjustment of the locations of the first and second apertures 25a, 25b on the first and second substrates 23a, 23b. For example, as shown in FIG. 5A, when viewed in the first direction D1, the first and second apertures 25a, 25b of the first and second substrates 23a, 23b may be placed at the same locations. In other words, when viewed in the first direction D1, the first apertures 25a of the first substrate 23a may be disposed to overlap the second apertures 25b of the second substrate 23b.

Alternatively, as shown in FIG. 5B, when viewed in a direction perpendicular to the substrate 23, the first and second apertures 25a, 25b of the first and second substrates 23a, 23b may be placed at different locations. In this case, the first and second substrates 23a, 23b may have different shapes so as not overlap each other where in FIG. 5B, the second apertures 25b appear with a dotted line shape. In other words, when viewed in the first direction D1, at least some of the first apertures 25a of the first substrate 23a may be disposed so as not to overlap at least some of the second apertures 25b of the second substrate 23b.

As shown in FIG. 5A and FIG. 5B, the first and second apertures 25a, 25b may be formed at the same location or at different locations, thereby allowing control of the flow velocity and flow rate of the air flowing through the first and second substrates 23a, 23b and the photocatalyst filter 10 therebetween.

Although the first and second apertures 25a, 25b on the first and second light sources 20a, 20b are illustrated as being formed at different locations in this embodiment, it should be understood that the present disclosure is not limited thereto and the number or diameter of the first and second apertures 25a, 25b on the first and second substrates 23a, 23b may be set differently.

Figure 6A:
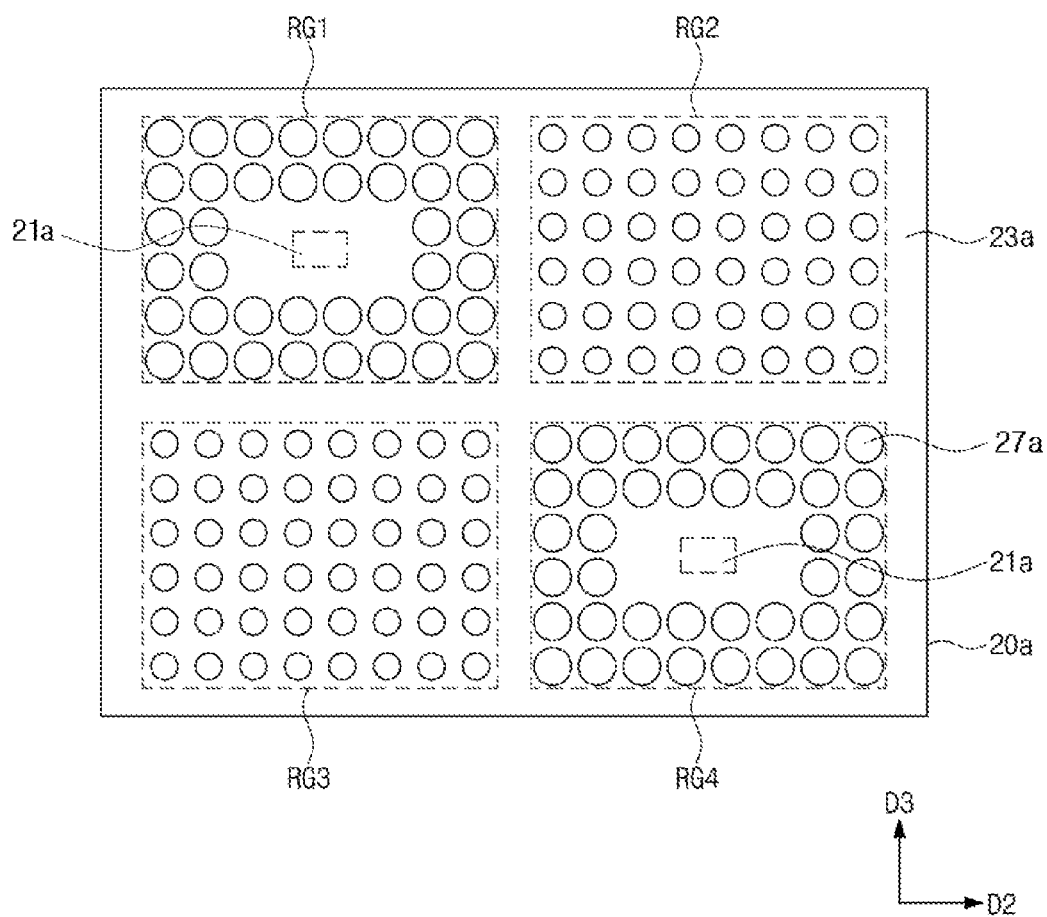
FIG. 6A is a plan view of modifications of the first light source in the air purification module shown in FIG. 4.
Figure 6B:
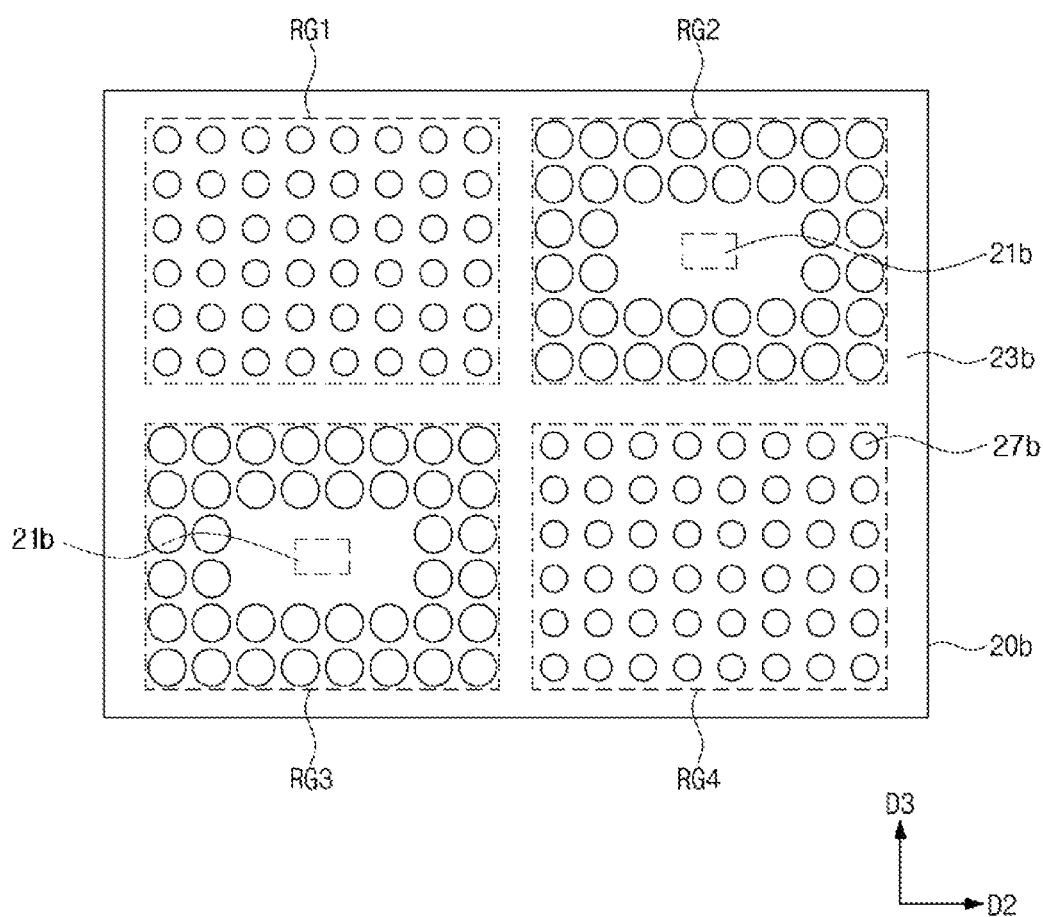
FIG. 6B is a plan view of modifications of the second light source in the air purification module shown in FIG. 4.

FIG. 6A and FIG. 6B are plan views of modifications of the first light source and the second light source in the air purification module according to the embodiment of the invention shown in FIG. 4, in which the first light source 20a and the second light source 20b are modified from the light sources 21a, 21b shown in FIG. 4.

In this embodiment, the number of light emitting devices 21a, 21b and irradiation regions RG1, RG2, RG3, RG4 may be combined in various ways. For example, as shown in FIGS. 6A and 6B, the first light source 20a is provided with two light emitting devices 21a and the second light source 20b is also provided with two light emitting devices 21b, in which the irradiation regions RG1, RG2, RG3, RG4 corresponding to the light emitting devices 21a, 21b may be set differently. As such, when the light sources are provided with multiple irradiation regions, the shape and arrangement of the irradiation regions may be modified in various ways depending on arrangement or irradiation angles of the light emitting devices. In this embodiment, the irradiation regions may be provided in a matrix of rows and columns.

In the embodiment, when viewed in the first direction D1, the first light source 20a and the second light source 20b are provided with multiple irradiation regions at locations thereof overlapping each other. That is, each of the first and second light sources 20a, 20b is provided with first to fourth irradiation regions RG1, RG2, RG3, RG4. The first to fourth irradiation regions RG1, RG2, RG3, RG4 may be provided in a 2×2 matrix of rows and columns. In this embodiment, the first to fourth irradiation regions RG1, RG2, RG3, RG4 may be arranged at a left upper end, a right upper end, a left lower end, and a right lower end, respectively.

Each of the first and second light sources 20a, 20b is provided with at least one light emitting device. For example, the first light source 20a is provided with two first light emitting devices 21a, which are placed corresponding to the first and fourth irradiation regions RG1, RG4. The second light source 20b is provided with at least two second light emitting devices, which are placed corresponding to the second and third irradiation regions RG2, RG3.

In the first and second light sources 20a, 20b, the first and second light emitting devices 21a, 21b may be disposed in various arrangements in the irradiation regions so as to allow uniform irradiation of the photocatalyst filter with a sufficient intensity of light. For example, when viewed in the first direction D1, at least one of the irradiation regions of the first light source 20a, in which the first light emitting device 21a is disposed, may not overlap at least one of the irradiation regions of the second light source 20b, in which the second light emitting device 21b is disposed. When the light emitting devices are disposed to face each other in the irradiation regions facing each other, there can be a significant uniformity difference in quantity (or intensity) of light between a portion at which the light emitting devices faces each other and a portion at which the light emitting devices do not face each other. When there is a significant uniformity difference, air treatment effects can be reduced in regions where a small quantity of light reaches. Accordingly, in order to allow each of the irradiation regions to be irradiated with light as uniformly as possible, the light emitting device may be provided only to one of the first light source 20a and the second light source 20b in the irradiation regions overlapping each other when viewed in the first direction D1. In this way, in the first light source 20a and the second light source 20b, the light emitting devices 21a, 21b are disposed so as not to overlap each other, whereby a uniform quantity of light can be supplied to the entirety of the photocatalyst filter 10.

In one embodiment, when a certain irradiation region is provided with the light emitting device, the irradiation region requires a portion for mounting the light emitting device and the apertures are not formed in the portion for mounting the light emitting device. Accordingly, the flow rate or velocity of air, on a portion at which the light emitting device is present, can become less than the flow rate or velocity of air on a portion at which the light emitting device is not disposed. To overcome this problem, in each of the light sources, the apertures in the regions where the light emitting devices are disposed may have different diameters than the apertures in the regions where the light emitting device is not disposed. For example, the apertures in the regions where the light emitting devices are disposed may have a greater diameter than the apertures in the regions where the light emitting device is not disposed.

In this embodiment, in the first light source 20a as shown in FIG. 6A, the first apertures 25a in the first and fourth irradiation regions RG1, RG4, in which the first light emitting devices 21a are disposed, may have a greater diameter than the first apertures 27a in the second and third irradiation regions RG2, RG3, in which the first light emitting device 21a is not disposed. Further, in the second light source 20b as shown in FIG. 6B, the second apertures 25b in the second and third irradiation regions RG2, RG3, in which the second light emitting devices 21b are disposed, may have a greater diameter than the first apertures 27b in the first and fourth irradiation regions RG1, RG4, in which the second light emitting device 21b is not disposed. As a result, the apertures in the regions where the light emitting devices 21 are disposed may have the same area as the apertures in the regions where the light emitting device 21 is not disposed. Further, although not identical, it is desirable that the diameters of the apertures be similar and a difference therebetween be about 20% or less.

In the regions where the light emitting devices 21 are disposed, the flow rate and the flow velocity of air in the apertures having a large diameter may be greater than those in the apertures having a small diameter, thereby compensating for reduction in area occupied by the apertures. Accordingly, it is possible to achieve uniform control of the flow rate and the flow velocity of air over the regions where the light emitting devices 21 are disposed and the regions where the light emitting device 21 is not disposed.

According to one embodiment, the air purification module may be provided with an air distributer 30 to provide a more uniform flow velocity and flow rate of air when air is supplied to the photocatalyst filter 10 in the first direction D1. The air distributer may be disposed at various locations. For example, the air distributer 30 may be disposed near the photocatalyst filter 10 or the light sources 20a, 20b. For example, the air distributer 30 may be provided to both side of the photocatalyst filter 10 outside the light sources 20a, 20b.

The air distributer 30 may be formed of a porous material that allows air to penetrate and distribute evenly. In other words, the air distributer 30 may be formed of a material having pores through which air passes. The air distributer 30 may be formed of, for example, non-woven fabrics, felt, ceramics, or organic polymers, such as porous PTFE. However, the material of the air distributer is not limited thereto so long as the air distributer has porosity to allow air to pass evenly therethrough.

The pores of the air distributer 30 may have various sizes and may have a smaller size than the diameter of the apertures in the light source. This structure is designed to achieve efficient distribution of the air passing through the air distributer.

In one embodiment, the air distributer 30 may have an antibacterial function. To this end, the air distributer 30 may include an organic antibacterial material and/or an inorganic antibacterial material. The inorganic antibacterial material may include, for example, silver nanoparticles.

With the structures described above, the air purification module according to the embodiments provides air to the photocatalyst filter at a uniform flow velocity through a uniform air flow channel, thereby enabling use of the entire region of the photocatalyst filter. As a result, the air purification module according to the embodiments can maximize sterilization/deodorization effects.

Figure 7:
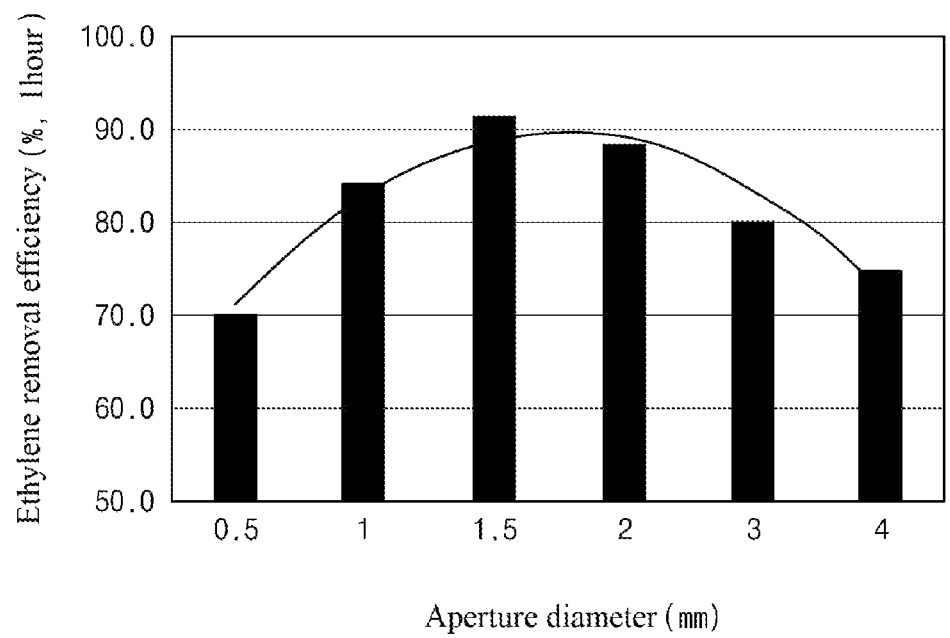
FIG. 7 is a graph depicting deodorization efficiency depending on the diameter of apertures in a substrate of a light source in an air purification module according to an embodiment of the present disclosure.
Figure 8:
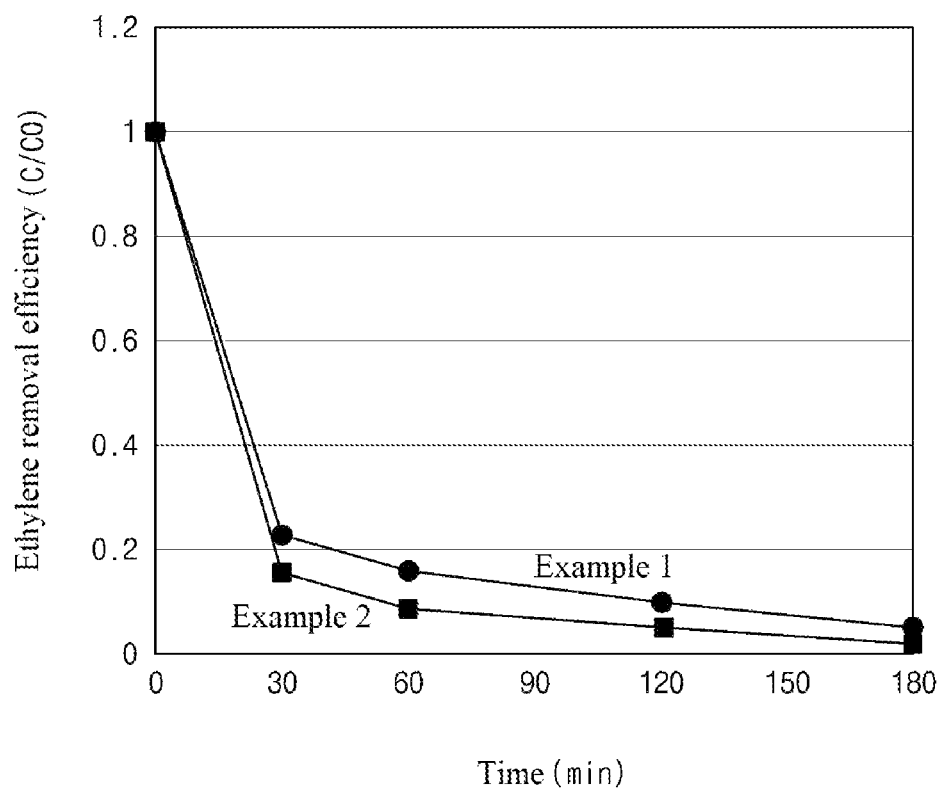
FIG. 8 is a graph depicting deodorization efficiency depending on the diameter of apertures in a substrate of a light source in an air purification module according to an embodiment of the present disclosure.

FIG. 7 and FIG. 8 are graphs depicting deodorization efficiency depending on the diameter of apertures in a substrate of a light source in an air purification module according to an embodiment of the present disclosure. In this embodiment, four light emitting diodes (IF=20 mA) configured to emit light having a wavelength of 365 nm were used as the light emitting devices, where IF is a forward current of the light emitting diodes. A single photocatalyst filter having a size of 33 mm (width)×33 mm (length)×8 mm (height) was used. The experiment was carried out in a 20 L chamber and a target substance to be deodorized was ethylene ($CH_2CH_2$), which was provided at an initial concentration of 50±5 ppm.

First, deodorization efficiency according to the aperture diameter of the light source substrate of the air purification module will be described. The deodorization efficiency differs according to the aperture diameter. Table 1 shows deodorization efficiency according to the aperture diameter of the light source substrate of the air purification module and FIG. 7 shows Table 1.

TABLE 1

| Aperture diameter (mm) | Ethylene removal efficiency (%) |
|---|---|
| 0.5 | 69.8 |
| 1 | 84.0 |
| 1.5 | 91.2 |
| 2 | 88.2 |
| 3 | 80.1 |
| 4 | 74.9 |

Referring to Table 1 and FIG. 7, depending on the diameter of the apertures, the deodorization efficiency increased and then decreased again at a certain point. That is, the deodorization efficiency increased from 0.5 mm to 1.5 mm in diameter of the apertures, and decreased again when the diameter of the apertures exceeded the upper limit of the diameter. Here, in particular, when the diameter of the apertures was in the range of 1 mm to 3 mm, the deodorization efficiency was higher than 75%. It is believed that, when the diameter of the apertures is less than about 1 mm, the flow rate of air becomes too low due to the small diameter of the apertures, causing deterioration in deodorization efficiency, and that, when the diameter of the apertures exceeds about 3 mm, deodorization becomes insufficient due to a rapid flow velocity, despite no reduction in flow rate of air due to the apertures. Referring to FIG. 8, it could be seen that, when the flow velocity was too slow, the deodorizing effect was deteriorated. Since the flow velocity is closely related to the diameter of the apertures, it could be seen that, if the diameter of the apertures was too small, the deodorization efficiency was rather deteriorated, despite reduction in flow velocity.

The air purification module according to the embodiments of the present disclosure may be employed by, in, or with various apparatuses.

Figure 9:
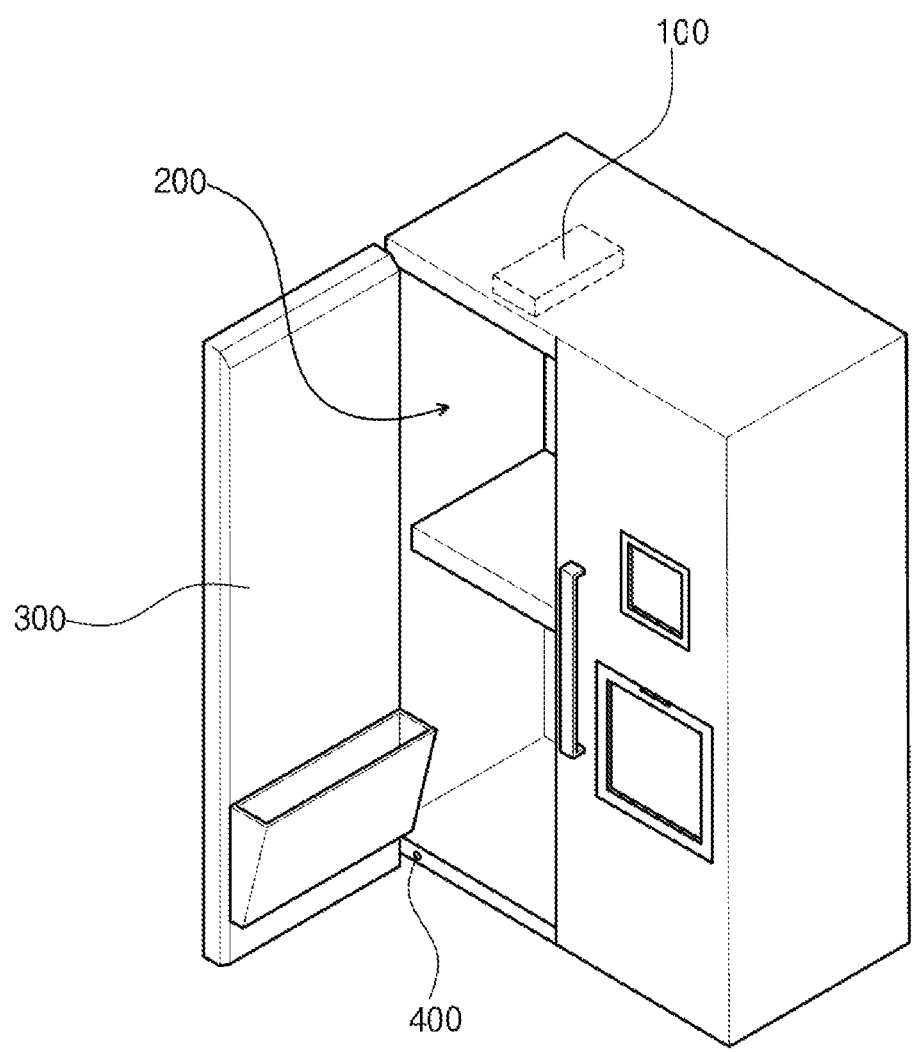
FIG. 9 is a perspective view of a refrigerator including an air purification module according to an embodiment of the present disclosure.

FIG. 9 is a view of a refrigerator including an air purification module according to one embodiment of the present disclosure. However, it should be understood that the air purification module according to the embodiments of the present disclosure may be applied not only to the refrigerator but also to other home appliances, furniture, and constructions, which require treatment of air, such as deodorization, purification, and the like.

A refrigerator 1000 according to one embodiment of the present disclosure may include a main body 200, which is provided with a cooler and has a storage compartment defined therein, and an air purification module 100 according to the above embodiments disposed in the storage compartment.

The main body 200 has at least one storage compartment and the air purification module may be disposed in a suitable region in the storage compartment.

The main body 200 is provided with at least one door 300 which opens or closes the storage compartment, and a sensor 400 disposed at one side of the main body 20 to face the door 300 and detecting whether the door is open or closed. The sensor 400 may be provided in the form of a switch that is pressed when the door is closed.

In the refrigerator 1000 according to this embodiment, when the door 300 is closed, the air purification module 100 may be turned on. When the air purification module 100 is turned on, air in the storage compartment is purified. If the door 300 is open, the air purification module 100 may be turned off.

Although some exemplary embodiments have been described herein, it should be understood by those skilled in the art that these embodiments are given by way of example only, and that various modifications, variations, and alterations can be made without departing from the spirit and scope of the present disclosure.

Therefore, the scope of the invention should be interpreted according to the following appended claims and equivalents thereto.

What is claimed is:

1. An air purification module, comprising:
a photocatalyst filter configured to purify air flowing therethrough; and
a light source sequentially arranged relative to the photocatalyst filter in a selected direction;
the light source being spaced apart from the photocatalyst filter and providing light to the photocatalyst filter, the light source comprising a substrate and a light emitting device disposed on the substrate,
wherein the substrate is disposed along a direction from the photocatalyst filter,
wherein the substrate further includes a photocatalyst-facing region corresponding to the photocatalyst filter and having first apertures and an outer region disposed outside the photocatalyst-facing region and having second apertures,
wherein a size of the first apertures is greater than a size of the second apertures.

2. The air purification module according to claim 1, wherein the photocatalyst filter has multiple through-holes parallel to a flow channel of the air and is disposed parallel to the aperture of the substrate.

3. The air purification module according to claim 2, wherein:
the through-holes pass through the photocatalyst filter in the selected direction, and
the aperture passes through the substrate in the selected direction, when viewed in the selected direction, the substrate has a larger area than the photocatalyst filter.

4. The air purification module according to claim 1, wherein at least part of the photocatalyst filter is disposed in an irradiation region to which light emitted from the light emitting device reaches.

5. The air purification module according to claim 4, wherein:
two or more apertures are provided and each aperture having a diameter ranging from 1.0 mm to 3.0 mm;
the substrate further comprises a heat dissipation portion disposed between irradiation regions and having no aperture; and
the irradiation regions are arranged in a matrix of rows and columns such that the heat dissipation portion is disposed between adjacent rows and between adjacent columns.

6. The air purification module according to claim 5, further comprising:
a housing receiving the photocatalyst filter and the light source and having apertures through which the air flows in the selected direction,
wherein the housing comprises a rib disposed at a location corresponding to the heat dissipation portion.

7. The air purification module according to claim 1, wherein the light source comprises a first light source and a second light source facing each other with the photocatalyst filter interposed therebetween.

8. The air purification module according to claim 7, wherein the light emitting devices of the first and second light sources face each other with the photocatalyst filter interposed therebetween, and each of the first light source and the second light source is provided with multiple apertures,
when viewed in the selected direction, the apertures of the first light source are disposed to overlap with the apertures of the second light source.

9. The air purification module according to claim 7, wherein the light emitting devices of the first and second light sources face each other with the photocatalyst filter interposed therebetween, and each of the first light source and the second light source is provided with multiple apertures;
when viewed in the selected direction, at least some apertures of the first light source do not overlap with at least some apertures of the second light source.

10. The air purification module according to claim 7, wherein the apertures of the first light source have a different size than the apertures of the second light source.

11. An air purification module, comprising:
a filter configured to purify air flowing therethrough;
a light source disposed spaced apart from the filter and comprising a first light source and a second light source that are configured to emit light having different wavelength bands including a UV wavelength band, wherein the filter and the light source are sequentially arranged in a direction;
an air distributer disposed adjacent to the filter or the light source to supply the air at a predetermined uniform flow velocity and at a predetermined uniform flow rate towards the filter in a direction,
wherein the first light source comprises a first substrate and one or more first light emitting devices disposed on the first substrate, and the second light source comprises a second substrate and one or more second light emitting devices disposed on the second substrate;

wherein the first substrate comprises at least one first aperture;

wherein the second substrate comprises at least one second aperture, wherein the air distributer has pores through which the air passes, an average diameter of the pores being smaller than a diameter of the at least one first aperture, a diameter of the at least one second aperture, or both.

12. The air purification module according to claim 11, wherein, when viewed in a selected direction perpendicular to the first light source and the second light source, the first light source further comprises a first set of regions and the second light source further comprise a second set of regions, the first set of regions and the second set of regions corresponding to and overlapping with each other in the selected direction, and the first light emitting devices are disposed in at least one of the first set of regions; and the second light emitting devices are disposed in in at least one of the second set of regions;

wherein, when viewed in the selected direction, said at least one of the first set of regions having the first light emitting device disposed, does not overlap said at least one of the second set of regions having the second light emitting device disposed.

13. The air purification module according to claim 12, wherein the at least one first aperture further comprises:

a third aperture present in said at least one of the first set of regions having the first light emitting devices disposed; and a fourth aperture present in another region of the first set of regions having no light emitting device;

wherein the third aperture has a different diameter than the fourth aperture, each of the third and the fourth apertures having a diameter ranging from 1.0 mm to 3.0 mm.

14. The air purification module according to claim 13, wherein, the diameter of the third aperture is larger than the diameter of the fourth aperture.

15. The air purification module according to claim 14, wherein a difference in area between the third aperture and the fourth aperture is 20% or less.

16. The air purification module according to claim 11, wherein the air distributer comprises an organic antibacterial material, an inorganic antibacterial material, or both.

17. A refrigerator comprising the air purification module according to claim 11.

* * * * *

UNITED STATES PATENT AND TRADEMARK OFFICE
CERTIFICATE OF CORRECTION

PATENT NO. : 11,931,490 B2  
APPLICATION NO. : 17/221413  
DATED : March 19, 2024  
INVENTOR(S) : Jae Hak Jeong et al.

Page 1 of 1

It is certified that error appears in the above-identified patent and that said Letters Patent is hereby corrected as shown below:

On the Title Page

In Item (30), under "Foreign Application Priority Data", include the foreign application priority data as follows:
"Nov. 29, 2018 (KR) ........................ 10-2018-0150412
Oct. 05, 2018 (KR) ........................ 10-2018-0119725"

Signed and Sealed this  
Twenty-seventh Day of August, 2024

Katherine Kelly Vidal  
*Director of the United States Patent and Trademark Office*